(12) United States Patent
Chacornac et al.

(10) Patent No.: US 8,383,146 B2
(45) Date of Patent: Feb. 26, 2013

(54) COMPOSITIONS FOR ORAL ADMINSTRATION OF ACTIVE PRINCIPLES REQUIRING MASKING OF TASTE

(75) Inventors: Isabelle Chacornac, Saint Romain de Jalionas (FR); Patricia Probeck, Lyons (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/360,151

(22) Filed: Jan. 27, 2012

(65) Prior Publication Data

US 2012/0121668 A1  May 17, 2012

Related U.S. Application Data

(60) Division of application No. 12/563,593, filed on Sep. 21, 2009, now abandoned, which is a continuation of application No. 12/139,778, filed on Jun. 16, 2008, now abandoned, which is a continuation of application No. 10/743,244, filed on Dec. 22, 2003, now abandoned.

(60) Provisional application No. 60/455,796, filed on Mar. 19, 2003.

(30) Foreign Application Priority Data

Dec. 23, 2002 (FR) ...................... 02 16521

(51) Int. Cl.
*A61K 9/14* (2006.01)
*A61K 9/28* (2006.01)

(52) U.S. Cl. ........................ 424/441; 424/489

(58) Field of Classification Search ........................ None
See application file for complete search history.

(56) References Cited

U.S. PATENT DOCUMENTS

| | | | | |
|---|---|---|---|---|
| 4,865,851 A * | 9/1989 | James et al. | ................ | 424/498 |
| 5,023,089 A * | 6/1991 | Sakamoto et al. | ........... | 424/502 |
| 5,188,838 A | 2/1993 | Deleuil et al. | | |
| 5,294,298 A | 3/1994 | Maesaka et al. | | |
| 5,380,532 A | 1/1995 | Deleuil et al. | | |
| 5,498,447 A * | 3/1996 | Nishii et al. | .................. | 427/213 |
| 5,707,646 A * | 1/1998 | Yajima et al. | ................. | 424/439 |
| 5,972,373 A * | 10/1999 | Yajima et al. | ................. | 424/439 |
| 6,136,347 A * | 10/2000 | Pollinger et al. | ............. | 424/495 |
| 6,209,479 B1 | 4/2001 | Walter et al. | | |
| 6,379,700 B2 * | 4/2002 | Joachim et al. | ............... | 424/468 |
| 6,475,510 B1 * | 11/2002 | Venkatesh et al. | ............ | 424/441 |
| 7,384,921 B2 * | 6/2008 | Tang et al. | ....................... | 514/29 |
| 2002/0022057 A1 * | 2/2002 | Battey et al. | ................... | 424/490 |
| 2005/0203035 A1 * | 9/2005 | Tang et al. | ....................... | 514/28 |
| 2006/0264386 A1 * | 11/2006 | Sun et al. | ......................... | 514/28 |
| 2007/0098843 A1 * | 5/2007 | Tomohira | .......................... | 426/5 |
| 2007/0231368 A1 * | 10/2007 | Wang et al. | ................... | 424/440 |
| 2008/0248105 A1 * | 10/2008 | Tang et al. | .................... | 424/456 |

FOREIGN PATENT DOCUMENTS

| | | |
|---|---|---|
| EP | 1161956 A1 | 12/2001 |
| EP | 0826376 B1 * | 4/2007 |
| JP | 2000103730 | 4/2000 |
| WO | WO 94/08576 | 4/1994 |

OTHER PUBLICATIONS

Kiyoji et al., Sustained Release Preparation and its Preparation, Patent Abstracts of Japan; Publication No. 50-122425, Publication Date: Jul. 14, 2984.

* cited by examiner

*Primary Examiner* — Robert A Wax
*Assistant Examiner* — Olga V Tcherkasskaya
(74) *Attorney, Agent, or Firm* — Ronald G. Ort

(57) ABSTRACT

A process for the preparation of a composition intended for the oral administration of active principles with unacceptable taste, which comprises from about 15% to about 30% of organoleptically unpleasant active ingredient (principle) that is mixed with from about 60% to about 80% of an ester of glycerol or of a fatty acid, to which a wax is optionally added and to which a surfactant is added, and in that it is prepared by a spray-cooling process which can produce a particle size of less than 350 μm.

12 Claims, No Drawings

COMPOSITIONS FOR ORAL ADMINSTRATION OF ACTIVE PRINCIPLES REQUIRING MASKING OF TASTE

FIELD OF THE INVENTION

The present invention relates generally to compositions intended for the oral administration of active principles with unacceptable taste, and also to the preparation thereof. In particular, the present invention relates to pharmaceutical compositions which by their nature exhibit bitter or bad tasting organoleptic characteristics.

BACKGROUND OF THE INVENTION

Some active principles exhibit unacceptable organoleptic properties and, as a result, are unsuitable for preparing pediatric or oral formulations intended for individuals in whom swallowing is difficult and can pose problems. For these reasons, some major products are deprived of a pediatric formulation and, in addition, some individuals are deprived of treatment using these active principles, which may have extremely prejudicial, or even vital, consequences.

The problem of masking taste has always been a considerable problem for the pharmaceutical industry. Antibiotics, often given to children for numerous childhood illnesses, are particularly plagued with this problem. Many systems have been tried, but in the case of active principles which are too bitter, coating systems have mostly proved to be insufficient and particulate systems, when they are more effective, exhibit drawbacks of too great a particle size, leading to a sandy aspect in the mouth and to the patient refusing the medicinal product.

In European patent EP 639365, a method has been described for preparing coated particles by spray-coating using a molten wax sprayed via a two-fluid nozzle. However, this method is based on spraying molten wax onto particles, so as to form a coating. No mixing of the active principle is carried out beforehand with the wax; in addition, the particles and the nozzle have large diameters. Finally, tests according to the method of the present invention, based only on the use of a molten wax, have not given acceptable results in terms of kinetics of release at pH=1.

It has now been found that compositions intended for oral administration can be developed and provide a masking of taste which is sufficient to be acceptable and to allow in particular the administration of pharmaceutical compositions to young children or to individuals not able to swallow.

SUMMARY OF THE INVENTION

The present invention comprises a taste masking formulation that eliminates or at least covers up the bad taste and/or unpleasant organoleptic sensory impression that are inherent in many pharmaceutical actives and antibiotics. The compositions according to the invention comprise from about 15 to about 30% of active ingredient (principle) mixed with from about 60% to about 80% of an ester of glycerol or of a fatty acid, to which a wax is optionally added, and to which a surfactant is added, and are prepared by a spray-cooling method which can produce a particle size of less than 350 μm.

DETAILED DESCRIPTION OF THE INVENTION

As described above, the present invention comprises a taste masking formulation that eliminates or at least covers up the bad taste and/or unpleasant organoleptic sensory impression (s) that are inherent in many pharmaceutical actives and antibiotics. The compositions according to the invention comprise from about 15 to about 30% of active ingredient (principle) mixed with from about 60% to about 80% of an ester of glycerol or of a fatty acid, to which a wax is optionally added, and to which a surfactant is added, and are prepared by a spray-cooling method which can produce a particle size of less than 350 μm.

Advantageously, the selection of esters of glycerol having a suitable pH-sensitivity profile allows release of the active principle at acid pH conditions as encountered in the stomach.

According to the invention, the esters of glycerol or of fatty acid used in the compositions according to the invention have the following characteristics: melting temperature in the range of from about 25° C. to about 100° C., preferably from about 25° C. to about 70° C. and stability in the molten state. The ester of glycerol may be chosen from glyceryl stearate or glyceryl palmitostearate, in particular Precirol®. The ester of glycerol is advantageously between 50 and 85% by weight of the total mixture of the composition; it is preferably between 60 and 80% by weight, and more particularly between 70 and 80% by weight.

The wax which can be optionally added may advantageously be carnauba wax, or it may also be chosen from paraffin or beeswax or candelilla wax. When a wax is added to the composition, it may be added in a proportion of from about 4% to about 10% by weight of the total mixture of the composition and in a ratio of from about 5% to about 20% with respect to the ester of glycerol introduced.

When a fatty acid is introduced into the composition, this fatty acid is advantageously chosen from palmitic, myristic or stearic acid. The fatty acid is introduced in a proportion of from about 60% to about 80% by weight of the total mixture of the composition.

The surfactant introduced into the composition is advantageously chosen from lecithins, in particular soybean lecithin, or surfactants of the family of sorbitan esters having an HLB of less than 7. The surfactant is added in a proportion of from about 1% to about 3% by weight of the total mixture of the composition.

Preferably, the diameters are advantageously less than 350 μm for more than 90% of the particles. More particularly, they may be between 100 μm and 350 μm for about 25% to about 65% of the particles and less than 100 μm for about 35% to about 75% of the particles.

According to the invention, the spray-cooling is carried out by spraying using a two-fluid nozzle to ensure that the desired particle size is obtained, i.e. a particle size of small diameter as described above.

According to the invention, the composition is prepared by mixing the active principle in the molten ester of glycerol, to which the other excipients have been added. The mixture is sprayed through the two-fluid nozzle at the top of a tower into which a cold gaseous counter-current is optionally introduced, intended to help the solidification of the sprayed droplets. The device is preferably equipped with a fluidized bed for recovering the particles and improving the rapidity of solidification.

The molten mixture introduced into the two-fluid nozzle is generally heated to between 60 and 100° C.

Preferably, the two-fluid nozzle advantageously comprises a diameter of 2.5 mm for the liquid section and a toric section of 0.3 mm for the air (or nitrogen) section. The flow rate of liquid and the flow rate of air (or of nitrogen) sprayed in the nozzle are fixed beforehand as a function of the diameters of the sections of the two-fluid nozzle used. Preferably, the flow rate of liquid is fixed at between 1 and 15 kg/h and the flow rate of air is fixed at between 2 and 5 m$^3$/h.

The particle size of the active principle mixed initially with the ester of glycerol ranges from about o about 350 µm. In certain cases, it may be necessary to carry out grinding before or after the mixing with the ester of glycerol and prior to the spraying. Preferably, the grinding is carried out dry, prior to the mixing. The tower used is a tower of the prilling tower type, but to which a two-fluid nozzle has been added (contrary to the conventional use of the prilling). The height of the tower is preferably between 2 and 8 m. The gaseous countercurrent intended for the cooling is advantageously a current of nitrogen or a current of dry gas. The flow rate depends on many factors, such as the temperatures, the chamber height, the amounts of product, etc. By way of indication, it may be fixed in particular between values: slightly above 0 and 350 Nm$^3$/h.

The composition may also contain other additives, such as sweeteners or taste enhancers (saccharinate, aspartame, glycerol, vanillin, menthol, etc., or any other substance conventionally used in the pharmaceutical industry), aromas, flow agents, lubricants, ballasts or mineral agents [silica, aluminum oxide, magnesium oxide, talc, etc., carbonates (calcium carbonate), phosphates (tricalcium phosphate), lactose, sorbitol, glycocoll, mannitol, glucose, maltodextrins, etc.], preserving agents (by way of example, sodium metabisulfite, propylene glycol, ethanol or glycerol), agents intended to modify the color. It is preferably a pharmaceutical composition.

The present invention relates to all active principles, alone or as mixtures, which can be administered orally and which exhibit organoleptic problems, the consequence of which is that they are unacceptable to individuals having to ingest them. The active principles are substances which are bitter, irritant, etc., or which have an unacceptable flavor. Said active principles are compatible with the ester of glycerol and its melting temperature.

In a nonlimiting manner, when the active ingredients (principles) are pharmaceutically active ingredients (principles), they may belong to any therapeutic classes, such as, for example, anti-bacterial agents [macrolides (spiramycin, ketolides such as for example telithromycin, etc.), streptogramins (pristinamycins such as pyostacin for example, virginiamycin for example), quinolones, etc.], antifungal agents (metronidazole, etc.), anti-parasitic agents (nivaquine, etc.), antiviral agents, anti-cancer agents, analgesics, non-steroidal anti-inflammatories, (NSAIDS), anti-tussins, psychotropic agents, steroids, medicinal products intended for the treatment of allergies, anti-asthmatics, antispasmodics, cardiovascular agents (roxitromycin for example etc.), therapeutic agents for the gastro-intestinal tract, etc.

They may also be active ingredients (principles), alone or as mixtures, intended for cosmetics, such as vitamins or plant or animal extracts.

The present invention has the advantage of an effective masking of taste coupled with a lack of or a very slight sandy feeling of the composition in the mouth.

Dissolution tests have been carried out and a test to slight dissolution at neutral pH, and therefore suitable masking of taste, and dissolution at levels of 80 to 100% at pH=1, after 60 minutes, attesting to the release of the active principle in the gastric environment.

The bitterness limit, as a function of the nature of the active principle, is measured. The attempts at dissolution are carried out in particular in a test for dissolution at neutral pH: glass of water test, at concentrations of 250 or 500 mg/l. The results are assessed with regard to the bitterness limit value evaluated. A dissolution approximately four times slower at neutral pH than at pH=1 is observed.

The kinetics of dissolution at pH=1 are measured for solutions with a concentration of 500 mg/l, in 0.1N HCl medium, in a dissolution medium containing 0.2% of sodium lauryl sulfate.

It will be appreciated that every suitable combination of the respective elements of the present invention may be interchanged with one or more of other similar, suitable components known in the art and changed in minor, non-functional respects. These additional embodiments of the invention are also regarded as falling within the scope of the claims herein. The examples detailed below are provided to better describe and more specifically set forth the elements and mechanics/operation of the present invention with reference to the drawings, but for obvious reasons cannot describe all of them. It is to be recognized that said examples therefore are for illustrative purposes only however, and should not be interpreted as limiting the spirit and scope of the invention as later recited by the claims that follow.

EXAMPLE 1

2 400 g of precirol melted beforehand in an incubator at 60° C. are introduced into a jacketed reactor, the set jacket temperature of which is fixed at 75° C. 78 g of soybean lecithin are added. When the soybean lecithin is dissolved, the set temperature is lowered to 65° C. and 540 g of pristinamycin are added. Stirring is carried out for 20 minutes at 300 rpm, and then the suspension is passed over a bore mill.

1 248 g of the ground suspension are then sprayed via a two-fluid nozzle in a prilling tower precooled with a current of cold nitrogen. At the beginning of spraying the temperature is 0° C. at the top of the tower and −20° C. at the bottom of the tower. The air pressure on the two-fluid nozzle is 1.5 bar, which produces a spray-air flow rate of 2.3 m$^3$/h. The flow rate of liquid is 4.7 kg/h.

At the end of spraying, the product is then fluidized for 20 minutes at −20° C., and then for 2 hours at 32° C.

The particle size of the product obtained, measured by sieving, is:

26% of particles between 0 and 100 µm
62% of particles between 100 and 315 µm
12% of particles between 315 and 500 µm
1% of particles greater than 500 µm.

The kinetics of dissolution at pH 1 are 92% in 60 minutes for the crude product and 99% in 60 minutes for the 100-315 µm particle size band.

The concentration of active material in the glass of water (neutral pH) is 182 mg/l after 5 minutes and 473 mg/l after 15 minutes for the crude granules. It is 89 mg/l after 5 minutes and 280 mg/l after 15 minutes for the granules of the 100-315 µm band.

EXAMPLE 2

704 g of precirol are introduced into a jacketed reactor, the set jacket temperature of which is fixed at 75° C. When the precirol is molten, 18 g of soybean lecithin are added. When the soybean lecithin is dissolved, 182 g of pristinamycin premicronized in an air jet micronizer, and exhibiting, after grinding, a median diameter of 2 µm, are added. Stirring is carried out for 45 minutes at 800 rpm in order to obtain a homogeneous suspension.

The suspension is then sprayed via a two-fluid nozzle in a prilling tower precooled with a current of cold nitrogen. At the beginning of spraying, the temperature is −14° C. at the top of the tower and −42° C. at the bottom of the tower. The air pressure on the two-fluid nozzle is 1.5 bar, which produces a spray-air flow rate of 2.3 m$^3$/h. The flow rate of liquid is 10.8 kg/h.

The particle size of the product obtained, measured by sieving, is:
- 30% of particles between 0 and 100 μm
- 54% of particles between 100 and 315 μm
- 11% of particles between 315 and 500 μm
- 5% of particles greater than 500 μm.

The kinetics of dissolution at pH 1 for the crude product are 86% in 60 minutes and 97% in 120 minutes.

The concentration of active material in the glass of water (neutral pH) is 22 mg/l after 5 minutes and 140 mg/l after 15 minutes for the crude granules.

EXAMPLE 3

907 g of precirol are added to a jacketed reactor, the set jacket temperature of which is fixed at 70° C. When the precirol is molten, 23 g of soybean lecithin are added. When the soybean lecithin is dissolved, 207 g of unground telithromycin exhibiting a median diameter of 114 μm are introduced. Stirring is carried out for 50 minutes at 500 rpm in order to obtain a homogeneous liquid: the telithromycin is visibly soluble in the precirol.

The suspension is then sprayed via a two-fluid nozzle in a prilling tower precooled with a current of cold nitrogen. At the beginning of spraying, the temperature is 0° C. at the top of the tower and −20° C. at the bottom of the tower. The air pressure on the two-fluid nozzle is 1.3 bar, which produces a spray-air flow rate of 4 m$^3$/h. The flow rate of liquid is 8.5 kg/h.

The particle size of the product obtained, measured by sieving, is:
- 59% of particles between 0 and 100 μm
- 38% of particles between 100 and 315 μm
- 3% of particles between 315 and 500 μm The kinetics of dissolution at pH 1 for the crude product are 98% in 60 minutes.

The concentration of active material in the glass of water (neutral pH) is 387 mg/l after 5 minutes and 873 mg/l after 15 minutes for the crude granules. It is 181 mg/l after 5 minutes and 475 mg/l after 15 minutes for the granules of the 100-315 μm band.

EXAMPLE 4

782 g of precirol and 115 g of carnauba wax are introduced into a jacketed reactor, the set jacket temperature of which is fixed at 95° C. When the fatty substances are molten, 23 g of soybean lecithin are added. When the soybean lecithin is dissolved, 230 g of unground telithromycin exhibiting a median diameter of 114 μm are introduced. Stirring is carried out for 60 minutes at 500 rpm in order to obtain a homogeneous liquid.

The suspension is then sprayed via a two-fluid nozzle in a prilling tower precooled with a current of cold nitrogen. At the beginning of spraying, the temperature is −7° C. at the top of the tower and −29° C. at the bottom of the tower. The air pressure on the two-fluid nozzle is 1.3 bar, which produces a spray-air flow rate of 4 m$^3$/h. The flow rate of liquid is 5 kg/h.

The particle size of the product obtained, measured by sieving, is:
- 27% of particles between 0 and 100 μm
- 50% of particles between 100 and 315 μm
- 16% of particles between 315 and 500 μm
- 7% of particles greater than 500 μm.

The kinetics of dissolution at pH 1 for the crude product are 77.5% in 60 minutes.

The concentration of active material in the glass of water (neutral pH) is 90 mg/l after 5 minutes and 340 mg/l after 15 minutes for the crude granules. It is 81 mg/l after 5 minutes and 658 mg/l after 15 minutes for the granules of the 100-315 μm band.

What is claimed is:

1. A process for the preparation of a particulate composition intended for the oral administration of a particulate active ingredient with unacceptable taste, comprising:
   mixing the particulate active ingredient in a molten ester of glycerol, wherein the ester of glycerol is present in an amount of between about 50% and about 85% by weight of the total composition;
   adding a lecithin as a surfactant in an amount of between about 1% and about 3% by weight of the total composition;
   optionally adding one or more excipients; and
   spray-cooling the resulting molten mixture using a device equipped with a two-fluid nozzle at the top of a tower into which a cold gaseous counter-current is introduced;
wherein the final particulate composition comprises more than 90% of the particles having a particle size of less than about 350 μm, and the dissolution rate of 80 to 100% in 60 min at pH 1.

2. The process as recited in claim 1, wherein the device is further equipped with a fluidized bed.

3. The process as recited in claim 1, wherein the ester of glycerol is glyceryl stearate or glyceryl palmitostearate.

4. The process as set forth in claim 1, wherein the active ingredient is a pharmaceutically active ingredient selected from the group consisting of anti-bacterial agents, antifungal agents, anti-parasitic agents, antiviral agents, anti-cancer agents, analgesics, non-steroidal anti-inflammatories, (NSAIDS), anti-tussives, psychotropic agents, steroids, antihistamines, anti-allergics, anti-asthmatics, anti-spasmodics, cardiovascular agents, anti-ulcer agents for the gastro-intestinal tract and mixtures thereof.

5. The process as recited in claim 1 wherein the active ingredient is an anti-bacterial agent.

6. The process as recited in claim 5 wherein the anti-bacterial agent is selected from the group consisting of macrolides, quinolones, streptogramins, and mixtures thereof.

7. The process as set forth in claim 6, wherein the anti-bacterial agent is a macrolide selected from spiramycin or a ketolide.

8. The process as set forth in claim 7, wherein the anti-bacterial agent is telithromycin.

9. The process as set forth in claim 1, wherein the ester of glycerol is present in an amount of between about 60% and about 80%.

10. The process as set forth in claim 9, wherein the ester of glycerol is present in an amount of between about 70% and about 85%.

11. The process as set forth in claim 1, wherein the molten mixture further comprises a wax.

12. The process as set forth in claim 1, wherein the particulate active ingredient is present in an amount of between about 15 and about 30% by weight of the total mixture of the composition.

* * * * *